United States Patent [19]

Hammond et al.

[11] 4,326,973

[45] Apr. 27, 1982

[54] QUATERNARY AMMONIUM SUCCINIMIDE SALT COMPOSITION AND LUBRICATING OIL CONTAINING SAME

[75] Inventors: Kenneth G. Hammond; Harry Chafetz, both of Poughkeepsie, N.Y.

[73] Assignee: Texaco Inc., White Plains, N.Y.

[21] Appl. No.: 224,728

[22] Filed: Jan. 13, 1981

[51] Int. Cl.³ .............................................. C10M 1/32
[52] U.S. Cl. .................. 252/34; 252/51.5 A; 546/283
[58] Field of Search ............ 252/51.5 A, 34; 546/283

[56] References Cited

U.S. PATENT DOCUMENTS

| | | |
|---|---|---|
| 3,272,746 | 9/1966 | Le Suer et al. .................... 252/34 X |
| 3,778,371 | 12/1973 | Malec ................................. 252/34 |
| 4,056,531 | 11/1977 | Malec ................................. 252/34 X |
| 4,108,858 | 8/1978 | Malec ................................. 252/34 X |
| 4,248,719 | 2/1981 | Chafetz et al. ..................... 252/34 |
| 4,251,380 | 2/1981 | Hammond et al. .................. 252/34 |
| 4,253,980 | 3/1981 | Hammond et al. .................. 252/34 |
| 4,273,663 | 6/1981 | Hammond et al. .................. 252/34 |

*Primary Examiner*—Andrew Metz
*Attorney, Agent, or Firm*—Carl G. Ries; Robert A. Kulason; James J. O'Loughlin

[57] ABSTRACT

A quaternary ammonium succinimide salt composition represented by the formula:

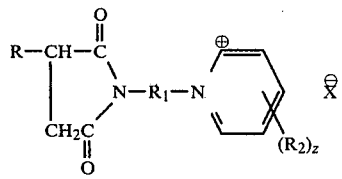

in which R is a hydrocarbyl radical having from 25 to 200 carbon atoms, $R_1$ is a divalent hydrocarbon radical having from 3–10 carbon atoms, $R_2$ is hydrogen or an alkyl radical having from 1 to 4 carbon atoms, z has a value from 0 to 5 and X is a halide radical is provided, as well as a method of preparation and a lubricating oil composition containing same.

14 Claims, No Drawings

QUATERNARY AMMONIUM SUCCINIMIDE SALT COMPOSITION AND LUBRICATING OIL CONTAINING SAME

BACKGROUND OF THE INVENTION

1. Field of the Invention

Internal combustion engines operate under a wide range of temperatures including low-temperature stop-and-go service as well as high temperature conditions produced by continuous high speed driving. Stop-and-go driving, particularly during cold, damp weather conditions, leads to the formation of sludge in the crankcase and in the oil passages of a gasoline engine. This sludge seriously limits the ability of the crankcase oil to lubricate the bearings and sliding wear surfaces in the engine or to act as a coolant. In addition, the sludge serves to contribute to rust formation within the engine because it tends to retain water in areas susceptible to corrosion. The noted problems are compounded by lubrication service maintenance recommendations calling for extended oil drain intervals.

It is known to employ nitrogen-containing dispersants and/or detergents in the formulation of crankcase lubricating oil compositions. Many of the known dispersant/detergent compounds are based on the reaction of an alkenylsuccinic acid or anhydride with an amine or polyamine to produce an alkenylsuccinimide or an alkenylsuccinamic acid as determined by selected conditions of reaction.

It is also known to chlorinate alkenylsuccinic acid or anhydride prior to the reaction with an amine or polyamine in order to produce a reaction product in which a portion of the amine or polyamine is attached directly to the alkenyl radical of the alkenylsuccinic acid or anhydride. The thrust of many of these processes is to produce a dispersant reaction product typically containing from about 0.5 to 5% nitrogen. These dispersant additives exhibited a high degree of oil solubility and have been found to be effective for dispersing the sludge that is formed under severe low temperature stop-and-go engine operating conditions. However, it has become increasingly difficult to formulate lubricants with these additives which meet the present requirements with respect to the prevention or inhibition of the formation of varnish.

Description of the Prior Art

A copending application Ser. No. 053,011, filed on June 28, 1979, and now U.S. Pat. No. 4,253,980, discloses a quaternary ammonium salt of an ester lactone and lubricants containing same.

A copending application, Ser. No. 053,010, filed on June 28, 1979, and now U.S. Pat. No. 4,251,380, discloses a quaternary ammonium diester salt composition and a hydrocarbon oil composition containing same.

A copending application, Ser. No. 093,481, filed on Nov. 13, 1979, and now U.S. Pat. No. 4,273,663 discloses a quaternary ammonium diester salt of a carboxylic compound and a lubricating oil composition containing same.

SUMMARY OF THE INVENTION

The quaternary ammonium succinimide salt composition of this invention is represented by the formula:

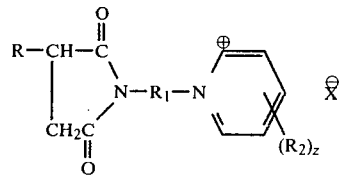

in which R is a hydrocarbyl radical having from 25 to 200 carbon atoms, $R_1$ is a divalent hydrocarbon radical having from 3-10 carbon atoms, $R_2$ is hydrogen or an alkyl radical having from 1 to 4 carbon atoms, z has a value from 0 to 5 and X is a halide radical.

The novel quaternary ammonium succinimide salt composition of the invention is prepared stepwise by reacting a hydrocarbon-substituted succinic anhydride with the prescribed amino alcohol to produce an intermediate N-(hydroxyalkyl)succinimide compound, followed by a reaction with an inorganic acid halide to form a second intermediate, namely, an N-(haloalkyl)-succinimide. This halide intermediate is finally reacted with a tertiary amine to form the prescribed quaternary ammonium salt dispersant of the invention.

The lubricating oil composition or lubricant concentrate of the invention comprises a substrate of lubricant viscosity and an effective dispersant amount of the prescribed quaternary ammonium succinimide salt of the invention.

DESCRIPTION OF THE PREFERRED INVENTION

The novel quaternary ammonium succinimide salt composition of the invention is represented by the formula:

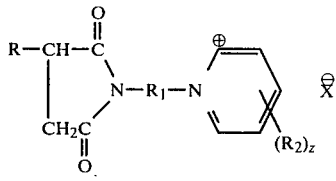

in which R, $R_1$, $R_2$, z and X have values indicated hereinabove. Hydrocarbyl is defined as a saturated or unsaturated monovalent hydrocarbon radical.

A preferred quaternary ammonium succinimide salt composition of the invention is one in which R is an alkenyl radical, such as a polybutenyl, polyisobutenyl and polypropenyl radical, having from about 50 to 125 carbon atoms, $R_1$ is a divalent hydrocarbon radical having from 3-5 carbon atoms $R_2$ is hydrogen or a methyl radical, z has a value from 0 to 2, and X is a chloride radical.

The preparation of the quaternary ammonium succinimide salt composition of the invention begins with a hydrocarbyl or alkenyl-substituted succinic anhydride. This starting reactant is represented by the formula:

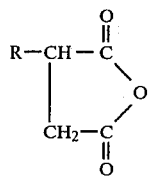

in which R has the value noted above. The method for preparing hydrocarbyl or alkenyl succinic anhydrides is well known in the art and does not constitute a part of this invention.

The hydrocarbyl succinic anhydride is reacted with a prescribed amino alcohol or alkanolamine to produce an intermediate N-(hydroxyalkyl)hydrocarbyl succinimide. Alkanolamines which can be employed in this reaction are represented by the formula:

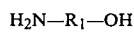

in which $R_1$, has the values indicated hereinabove. Typical amino alcohols which are useful for preparing effective dispersants of this invention include 3-aminopropanol, 3-amino-2-methylpropanol, 3-amino-2,2-dimethylpropanol, 3-amino-2,3-dimethylpropanol, 4-aminobutanol, 4-amino-2-methylbutanol, 4-amino-3-methylbutanol, 3-aminobutanol, 3-amino-2-methylbutanol, 3-amino-3-methylbutanol, 3-aminopentanol, 4-aminopentanol and 5-aminoptentanol.

In contrast to the prescribed aminoalkanols, the quaternary ammonium compounds prepared from aminoethanol are relatively ineffective.

In general, this reaction is conducted by dissolving the hydrocarbylsuccinic anhydride and the aminoalkanol in an inert solvent, such as a hydrocarbon solvent, i.e. heptane, benzene, toluene, xylene, etc. and refluxing the mixture until the conversion to the succinimide is essentially complete. This reaction is conveniently conducted at an elevated temperature, preferably at the reflux temperature of the solvent employed for a sufficient length of time to effect the desired succinimide formation.

The intermediate N-(hydroxyalkyl)hydrocarbylsuccinimide is reacted with an inorganic acid halide to form a second intermediate product. Suitable inorganic acid halides include phosphorus trichloride, phosphorus pentachloride, phosphorus tribromide, thionyl halides, such as thionyl chloride and thionyl bromide, hydrogen halides, such as hydrochloric acid, hydrobromic acid and hydroiodic acid. This reaction is generally conducted by dissolving the intermediate N-(hydroxyalkyl)-hydrocarbyl-substituted succinimide compound in an inert solvent, preferably a hydrocarbon solvent and adding the prescribed inorganic halide to the reaction mixture. This reaction is exothermic and must be initiated and conducted using a moderate reaction temperature. In general, this reaction can be conducted at temperatures ranging from about 10° C. up to about 75° C. to produce the second intermediate reaction product, namely, the N-(haloalkyl)-hydrocarbyl-substituted succinimide.

In the final step of the reaction, the N-(haloalkyl)-hydrocaryl-substituted succinimide is reacted with a tertiary heteroaromatic amine in order to form the prescribed quaternary ammonium succinimide salt composition. The effective tertiary heteroaromatic amine is represented by the formula:

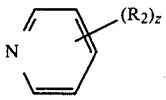

in which $R_2$ is hydrogen or an alkyl radical having from 1 to 4 carbon atoms and z is a number from 0 5. Examples of suitable tertiary heteroaromatic amines include pyridine, 2-methylpyridine, 2,3-dimethylpyridine, and 4-methylpyridine.

In general, the second intermediate reaction product is dissolved in an inert solvent such as a hydrocarbon diluent oil. The reactants are stirred or agitated at an elevated temperature for sufficient time to effect the formation of the desired quaternary ammoniumhydrocarbylsubstituted succinimide salt.

The following examples illustrate the method for preparing the quaternary ammonium succinimide salt composition of the invention.

EXAMPLE I

A mixture containing polybutenyl (1300 MW) succinic anhydride (53.5 Sap. No., 1050 gr., 0.50 mole), 3-aminopropanol (37.5 gr., 0.50 mole) and toluene 600 ml. was stirred at reflux for 12 hours during which time water was continuously removed from the mixture in a Dean Stark collector. The mixture was then stripped to 90° C. (1 mm.) to yield 1089 gr. of a succinimide intermediate product. This intermediate, N-(3-hydroxylpropyl)polybutenyl (1300 MW) succinimide was analyzed and found to contain 0.57 weight percent nitrogen vs. 0.63% theory.

A mixture containing the above intermediate (196 gr., 0.1 mole OH) and 200 ml. of toluene was stirred at room temperature as thionyl chloride (24.5 gr., 0.21 mole) was added slowly over approximately a 10 min. period. The mixture was then heated at 70° C. for 4 hours, allowed to cool, diluted with a small amount of water, and stripped to 90° C. (3 mm. Hg) to yield a chlorinated intermediate product. Analysis of this product, N-(3-chloropropyl)polybutenyl (1300 MW) succinimide, gave the results 1.65 wt. % chlorine. vs. 1.60% of theory.

A mixture containing the immediately preceeding intermediate product (50 gr.), 4-picoline (50 ml.) and diluent oil (50 gr.) was stirred at 130° C. for 7.5 hr. The mixture was diluted with heptane, filtered through filter cell and then stripped to 90° C. (2 mm. Hg) to yield 95 gr. of a quaternary ammonium salt product analyzing 0.68 wt. % nitrogen vs. 0.77% theory and 0.65 wt. % chlorine. vs. 0.60% theory corresponding to the compound N-(3-polyisobutenylsuccinimidopropyl)-4-methylpyridinium chloride.

EXAMPLE II

The compound N-(4-polyisobutenylsuccinimidobutyl)-pyridinium chloride is prepared by following the procedure of Example I using 4-aminobutanol as the amino alcohol and pyridine as the tertiary heteroaromatic amine.

EXAMPLE III

The compound N-(5-polyisobutenylsuccinimidopentyl)-4-methylpyridinium chloride is prepared by following the procedure of Example I using 5-aminopentanol as the amino alcohol and 4-methylpyridine as the tertiary heteroaromatic amine.

Other quaternary ammonium succinimide salt compositions of the invention prepared by following the procedure of Example I include those derived from 3-amino-2-methylpropanol, 3-amino-2,2-dimethylpropanol, 3-amino-2,3-dimethylpropanol, 4-amino-2-methylbutanol, 4-amino-3-methylbutanol, 3-aminobutanol, 3-amino-2-methylbutanol, 3-aminopentanol and 4-aminopentanol.

The lubricant composition of the invention comprises a major amount of a mineral hydrocarbon oil or synthetic oil of lubricating viscosity and an effective detergent-dispersant amount of the prescribed quaternary ammonium salt. Advantageously, in the finished lubricating salt oil composition, the prescribed quaternary ammonium salt content ranges between about 0.1 and 10 percent by weight, preferably between about 0.5 and 5 weight percent. In the lubricating oil concentrates, from which the finished lubricating compositions are derived via the addition of added lubricating oil, quaternary ammonium salt contents between about 10 and 50 weight percent are found. Thus, concentrations of the additive in lubricating oils and lubricating oil concentrates range from 0.1 to 50 weight percent.

The hydrocarbon oil in the finished lubricating composition advantageously constitutes at least about 85 weight percent and preferably between about 90 and 98 weight percent of the composition, and in the lube oil concentrates between about 50 and 90 weight percent of the composition. It is to be noted that even in the lubricating oil concentrates the prescribed quaternary ammonium salt will exhibit detergent-dispersancy.

Examples of the hydrocarbon base oil contemplated herein are the naphthenic base, paraffinic base and mixed base mineral oils, lubricating oils derived from coal products and synthetic oils, e.g., alkylene polymers such as polypropylene and polyisobutylene of a molecular weight of between about 250 and 2500. Advantageously, a lubricating base oil having a lubricating oil viscosity at 100° F. of between about 50 and 1000, preferably between about 100 and 600, are normally employed for the lubricant compositions and concentrates thereof (SUS basis).

In the contemplated finished lubricating oil compositions other additives may be included in addition to the dispersant of the invention. The additives may be any of the suitable standard pour depressants, viscosity index improvers, oxidation and corrosion inhibitors, anti-foamants, supplementary detergent-dispersants, etc. The choice of the particular additional additives to be included in the finished oils and the particular amounts thereof will depend on the use and conditions desired for the finished oil product.

Specific examples of the supplementary additives are as follows:

The widely used and suitable VI improver is the polymethacrylate having the general formula:

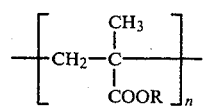

where R is an aliphatic radical of from 1 to 20 carbons and n is an integer of between about 600 and 35,000. One of the most suitable VI improvers is the tetrapolymer of butyl methacrylate, dodecyl methacrylate, octadecyl methacrylate, and dimethylaminoethyl methacrylate having a respective component weight ratio in the polymer of about 4:10:5:1 in admixture with oil comprising about 40 weight percent tetrapolymer and 60 percent oil. Another VI improver is a copolymer of ethylene and propylene having a molecular weight of 20,000 to 50,000 containing 30 to 40 percent propylene in the copolymer in admixture with oil comprising 13 weight percent copolymer and 87 weight percent oil. The VI improvers are normally employed in the finished lubricant compositions in quantities between about 0.1 and 10 percent by weight.

One of the commonly employed lube oil corrosion inhibitors and antioxidants are the divalent dialkyl dithiophosphates resulting from the neutralization of a $P_2S_5$-alcohol reaction product with a divalent metal or divalent metal oxide. Barium and zinc dialkyl dithiophosphate are specific examples. Another class of antioxidants are the polyalkylated diphenylamines, such as a mixture of 2,2'-diethyl-4,4'-dioctyldiphenylamine and 2,2'-diethyl-4-octyldiphenylamine. The corrosion and oxidation inhibitors are usually present in the finished lubricating oil compositions in concentrations of between about 0.1 and 3 weight percent.

Examples of supplementary detergent-dispersants which can be employed are the monoethoxylated inorganic phosphorus acid-free, steam hydrolyzed polyalkylene (500–50,000 MW)-$P_2S_5$ reaction product, alkaline earth metal alkylphenolates, such as barium nonylphenolate, barium dodecylcresolate, calcium dodecylphenolate and the calcium carbonate overbased calcium alkaryl sulfonates formed by blowing a mixture of calcium hydroxide and a calcium alkaryl sulfonate, e.g., calcium alkyl benzene sulfonate of about 900 m.w. with carbon dioxide to form a product having a total base number (TBN) of 50 or more, e.g., 300 to 400.

If antifoamants are employed in the finished compositions, one widely used class which is suitable are the dimethyl silicone polymers employed in amounts of between about 10 and 1000 ppm.

The following test was employed to determine the dispersant effectiveness of the lubricant composition of the invention.

BENCH VC TEST

In the Bench VC Test, a mixture containing the test oil and a diluent are heated at an elevated temperature. After heating, the turbidity of the resultant mixture is measured. A low % turbidity (0–10) is indicative of good dispersancy while high results (20–100) are indicative of oils of increasingly poor dispersancy.

EXAMPLE IV

A fully formulated SAE Grade 10W-40 lubricating oil composition containing the quaternary ammonium salt of the invention was tested for its dispersant effectiveness in the Bench VC Test in comparison to a fully formulated base oil without theA amine salt dispersant, and to fully formulated lubricating oil compositions containing either a commercial succinimide dispersant or an intermediate product.

The base blend employed contained the following conventional additives:

0.15 weight % zinc as zinc dialkyldithiophosphate 0.23 weight % calcium as overbased calcium sulfonate 0.25 weight % alkylated diphenylamine antioxidant 11.5 weight % ethylene-propylene copolymer VI improver
0.15 weight % ethoxylated alkylphenol
0.10 weight % methacrylate pour depressant
150 ppm silicone antifoamant mineral oil—balance (viscosity SUS at 100° F. at 120)

The quaternary ammonium salt dispersant of the invention was added to the base blend at three concentration levels and then tested in the Bench VC Test.

The results are set forth in the table below:

TABLE I

BENCH VC TEST

| Run | Wt. % of Additive in Base Blend[1] | | Turbidity |
|---|---|---|---|
| 1 | Base Blend (no dispersant) | | 97.5 |
| 2 | N-(3-Hydroxypropyl)polybutenyl (1300 MW) succinimide Intermediate, | 4% | 75.5 |
| 3 | N-(3-Hydroxypropyl)polybutenyl (1300 MW) succinimide Intermediate, | 6% | 69.0 |
| 4 | N-(3-Hydroxypropyl)polybutenyl (1300 MW) succinimide Intermediate, | 8% | 75.0 |
| 5 | N-(3-Chloropropyl)polybutenyl (1300 MW) succinimide Intermediate, | 4% | 91.0 |
| 6 | N-(3-Chloropropyl)polybutenyl (1300 MW) succinimide Intermediate, | 6% | 92.0 |
| 7 | N-(3-Chloropropyl)polybutenyl (1300 MW) succinimide Intermediate, | 8% | 94.0 |
| 8 | Quaternary Ammonium Salt Product of Example I, | 4% | 27.0 |
| 9 | Quaternary Ammonium Salt Product of Example I, | 6% | 3.5 |
| 10 | Quaternary Ammonium Salt Product of Example I, | 8% | 2.0 |
| 11 | Commercial Dispersant, | 4% | 26.0 |
|  | " | 6% | 6.0 |
|  | " | 8% | 3.5 |

[1]The additives were 50% concentrates in diluent oil.

The foregoing tests demonstrate that the prescribed quaternary ammonium salts of the invention are excellent dispersants for lubricating oil compositions exhibiting an effectiveness equal or superior to that of a commercial lubricating oil dispersant.

We claim:

1. A quaternary ammonium succinimide salt composition represented by the formula:

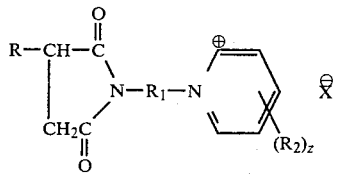

in which R is a hydrocarbyl radical having from 25 to 200 carbon atoms, $R_1$ is a divalent hydrocarbon radical having from 3 to 10 carbon atoms, $R_2$ is hydrogen or an alkyl radical having from 1 to 4 carbon atoms, z has a value from 0 to 5 and X is a halide radical.

2. A quaternary ammonium succinimide salt composition according to claim 1 in which R is a hydrocarbon radical having from 50 to 125 carbon atoms, z has a value from 0 to 2, and X is a chloride or bromide anion.

3. A quaternary ammonium succinimide salt composition according to claim 1, in which $R_2$ represents hydrogen or a methyl radical.

4. A quaternary ammonium salt salt composition represented by the formula:

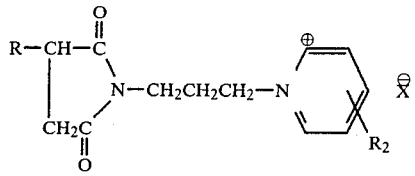

in which R is a hydrocarbyl radical having from 25 to 200 carbon atoms, $R_2$ is hydrogen or a methyl radical and X is a chloride anion.

5. The compound N-(3-polyisobutenylsuccinimidopropyl)-4-methylpyridinium chloride.

6. The compound N-(4-polyisobutenylsuccinimidobutyl)pyridinium chloride.

7. The compound N-(5-polyisobutenylsuccinimidopentyl) 4-methylpyridinium chloride.

8. A lubricating oil composition comprising a major portion of a mineral lubricating oil and a minor dispersant amount of a quaternary ammonium succinimide salt composition represented by the formula:

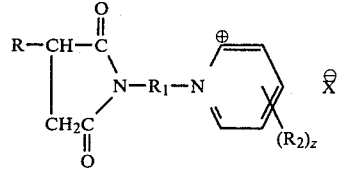

in which R is a hydrocarbyl radical having from 25 to 200 carbon atoms, $R_1$ is a divalent hydrocarbon radical having from 3–10 carbon atoms, $R_2$ is hydrogen or an alkyl radical having from 1 to 4 carbon atoms, z has a value from 0 to 5 and X is a halide radical.

9. A lubricating oil composition comprising a major portion of a mineral lubricating oil and a minor dispersant amount of a quaternary ammonium succinimide salt composition according to claim 8 in which R is a hydrocarbon radical having from 50 to 125 carbon atoms, and X is a chloride or bromide anion.

10. A lubricating oil composition comprising a major portion of a mineral lubricating oil and a minor dispersant amount of a quaternary ammonium succinimide salt composition according to claim 8, in which $R_2$ is hydrogen or a methyl radical.

11. A lubricating oil composition comprising a major portion of a mineral lubricating oil and a minor dispersant amount of a quaternary ammonium salt composition represented by the formula:

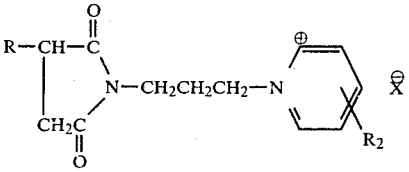

in which R is a hydrocarbyl radical having from 25 to 200 carbon atoms, $R_2$ is hydrogen or a methyl radical and X is a chloride anion.

12. A lubricating oil composition according to claim 8 in which said dispersant is N-polyisobutenylsuccinimidopropyl)-4-methylpyridinium chloride.

13. A lubricating oil composition according to claim 8 in which said dispersant is N-(4-polyisobutenylsuccinimidobutyl)pyridinium chloride.

14. A lubricating oil composition according to claim 8 in which said dispersant is N-(5-polyisobutenylsuccinimidopentyl)-4-methylpyridinium chloride.

* * * * *